United States Patent [19]

Abele et al.

[11] Patent Number: 5,151,100
[45] Date of Patent: Sep. 29, 1992

[54] HEATING CATHETERS

[75] Inventors: John E. Abele, Concord, Mass.; Charles E. Lennox, Hudson, N.H.; Paul C. Nardella, Easton; Sharad H. Joshi, Norwood, both of Mass.

[73] Assignee: Boston Scientific Corporation, Watertown, Mass.

[21] Appl. No.: 547,931

[22] Filed: Jul. 3, 1990

Related U.S. Application Data

[63] Continuation-in-part of Ser. No. 263,815, Oct. 28, 1988, Pat. No. 4,955,377.

[51] Int. Cl.⁵ .............................................. A61B 17/36
[52] U.S. Cl. ..................................... 606/28; 128/401; 128/786
[58] Field of Search ................... 606/27-31; 128/399-403, 784-786, 804

[56] References Cited

U.S. PATENT DOCUMENTS

| | | | |
|---|---|---|---|
| 4,747,405 | 5/1988 | Leckrone | 606/7 |
| 4,754,752 | 7/1988 | Ginsburg et al. | 128/401 |
| 5,019,075 | 5/1991 | Spears et al. | 606/7 |

FOREIGN PATENT DOCUMENTS

| | | |
|---|---|---|
| 0251745 | 1/1988 | European Pat. Off. |
| 0370890 | 5/1990 | European Pat. Off. |
| 9014046 | 11/1990 | World Int. Prop. O. |
| 9103996 | 4/1991 | World Int. Prop. O. |

OTHER PUBLICATIONS

510 (K) Notification; ACMI Bipolar Hemostatic Electrode; Cat. No. 9140; 1980.
Circulation Supplement; Abstracts from the 61st Scientific Sessions; II-296; 1181; 1988.
Astrahan et al.; Temp. Meas. From MV Antenna; Figure Captions; 1988.
Brezovich et al.; Radiation Oncology Biology-Physics 7:423-430; 1981.
Small Business Innovation Reasearch Program; Luxtron Corp.; 1984.
Protell et al.; Gastroenterology; 74:257-262; 1978.
Samaras et al.; Med. Phys; 10:326-332; 1983.
Szwarnoski; Clin. Phys. Physiol. Meas.; 4:79-84; 1983.
Trembly et al.; Proc. of the Tenth Annual Northeast Bioengineering Conf.; pp. 105-108; 1982.

*Primary Examiner*—Peter A. Aschenbrenner
*Attorney, Agent, or Firm*—Fish & Richardson

[57] ABSTRACT

A catheter device and method for heating tissue, the device having a catheter shaft constructed for insertion into a patient's body, and at least one chamber mounted on the catheter shaft. The catheter shaft has at least one lumen for fluid flow through the shaft. The chambers are defined by walls that are at least in part expandable. Fluid flows, through the lumens, between the chambers and a fluid source outside the body. The chambers can be filled with the fluid after they have been placed within the body. A heating device heats liquid within at least one of the chambers, so that heat is transmitted from the liquid to surrounding tissue by thermal conduction through the wall of the chamber. Means are provided for selectively directing heat transmission toward a selected portion of surrounding tissue. The chambers are fillable with fluid separately from each other, so that the chambers can occupy any of a plurality of possible total volumes. By selecting the total volume of chambers, compression of the tissue can be controlled, and hence the effectiveness of transfer of heat to the tissue can be controlled. According to the method, the catheter device is used to heat tissue from within a duct in a patient's body. The chambers are inserted into the duct and filled with fluid. Liquid is heated within at least one of the chambers, and heat is selectively directed toward a selected portion of surrounding tissue.

37 Claims, 10 Drawing Sheets

HEATING CATHETERS

This application is a continuation-in-part of U.S. application Ser. No. 07/263,815, filed Oct. 28, 1988, now U.S. Pat. No. 4,955,377.

BACKGROUND OF THE INVENTION

This invention relates to heating catheters, and especially to balloon catheters and similar devices used to apply heat within a patient's body, for hyperthermic treatment of tumors and other medical procedures.

Certain lesions, such as tumors or plaque deposits located in or near various ducts of the body, are positioned eccentrically, rather than concentrically, with respect to the duct. For example, a tumor of the esophagus might be located eccentrically on one side of the esophagus. Such a tumor might typically be treated by inserting a balloon catheter into the esophagus and heating fluid inside the balloon.

The extent of heating of tissue is a function of the amount of compression of the tissue. As tissue is compressed, it loses its ability to act as a heat sink, and hence the temperature of the compressed tissue increases. The amount of compression of the tissue is dependent upon the volume occupied by the balloon relative to the diameter of the vessel or duct. The compression of the tissue is not necessarily dependent upon the pressure inside the balloon, however, because the pressure inside the balloon is a consequence of the resistance of the balloon itself to expansion, especially if the balloon is nondistensible, rather than a consequence of the resistance of the tissue to expansion of the balloon.

SUMMARY OF THE INVENTION

The invention features catheter devices for use in hyperthermia treatment of esophageal tumors and other benign or malignant tumors, as well as catheter devices for use in blood vessel applications.

In one aspect the invention features a catheter device for heating tissue, employing a catheter shaft constructed for insertion into a patient's body, and at least one chamber mounted on the catheter shaft. The catheter shaft has at least one lumen for fluid flow through the shaft. The chamber or chambers are defined by walls that are at least in part expandable to engage body tissue. Fluid can flow through the lumen between the chamber or chambers and a fluid source outside the body. The chamber or chambers can be filled thereby with the fluid after they have been placed within the body. A heating device can heat liquid within at least one of the chambers to a controlled temperature. Means are provided for selectively directing heat transmission, by thermal conduction through the wall of the heated chamber, from the liquid in the balloon toward a portion of surrounding tissue.

In preferred embodiments, the heating device consists of a plurality of spaced electrical contacts enclosed within the heated chamber, and corresponding conductors for connecting the electrical contacts to a power supply that applies a radio frequency electrical potential to the contacts. The heating device is adapted to operate with liquid within the heated chamber that is electrically conductive and preselected to produce resistive heating. The contacts are exposed to the liquid space of the heated chamber, so that the radio frequency electrical potential can cause current to flow through liquid between the contacts. The heated chamber and the contacts are cooperatively constructed and arranged to cause the current to be substantially confined to liquid within the heated chamber. The liquid is heatable on the bases of $I^2R$ losses of the radio frequency electric current flowing between the electrical contacts. The means for selectively directing heat transmission is at least one nonheated chamber mounted adjacent to the heated chamber in a position to engage at least part of the tissue surrounding the catheter device. The heated and nonheated chambers are disposed at differing positions radially upon the catheter shaft. The nonheated chamber is fillable with fluid. The catheter device employs a power supply constructed to operate at a frequency between 100 KHz and 1 MHz. Means are provided for monitoring the temperature of the liquid within the heated chamber, and a temperature control circuit controls the output of the power supply in response to information received from the temperature monitor.

In another preferred embodiment one heated and two nonheated chambers are disposed at differing positions longitudinally, rather than radially, along the catheter shaft. One unheated chamber is disposed distal to the heated chamber along the catheter shaft, and at least one unheated chamber is disposed proximal to the heated chamber along the catheter shaft. In another embodiment the catheter device employs an auxiliary heating device that heats liquid within a chamber not heated by the other heating device, so that heat transmission can be selectively directed by selecting one of the chambers for heating, or so that both chambers can be heated to differing temperatures. In another embodiment an unheated chamber is disposed within the heated chamber. In another embodiment the means for selectively directing heat transmission is a heat-insulating or heat-reflective material applied to a portion of the wall of the heated chamber to make that portion of the wall of the heated chamber resistant to heat transmission In another embodiment a heat-insulating or heat-reflective material is applied to the wall of the nonheated chamber or chambers, to make the wall of the nonheated chamber or chambers resistant to heat transmission. In another embodiment, the means for selectively directing heat transmission is a means for inserting a bubble of thermally insulating gas into the heated chamber. In another embodiment, at least one of the chambers is associated with more than one lumen of the catheter device for cooling fluid flow between the chamber and a fluid source outside the body.

The selective directing of heat transmission into the surrounding tissue according to the invention allows for hyperthermia treatment of lesions located eccentrically on ducts in the body, such as tumors of the esophagus, while isolating healthy tissue from heat, which can cause the esophagus to fall apart or otherwise damage healthy tissue. The embodiment of the invention in which multiple chambers are disposed axially along the catheter shaft can be used in blood vessel applications for heating tissue radially while avoiding heating of blood in the axial direction.

In another aspect the invention features a catheter device for heating tissue, employing at least two chambers mounted on the catheter shaft. The catheter shaft has at least two lumens for fluid flow through the shaft. Each of the chambers is associated with at least one lumen for fluid flow between the chamber and a fluid source outside the body. A heating device causes at least a portion of the tissue surrounding the chambers to be heated. At least one of the chambers is fillable with fluid separately from at least one other chamber, so that the chambers together can occupy any of a plurality of possible total volumes. By selecting the total volume of all of the chambers, the compression of the tissue can be controlled, and hence the effectiveness of transfer of heat to the tissue can be controlled. In preferred embodiments all of the chambers have substantially similar dimensions.

DESCRIPTION OF THE PREFERRED EMBODIMENT

We first briefly describe the drawings.

DRAWINGS

STRUCTURE

Figure 1:
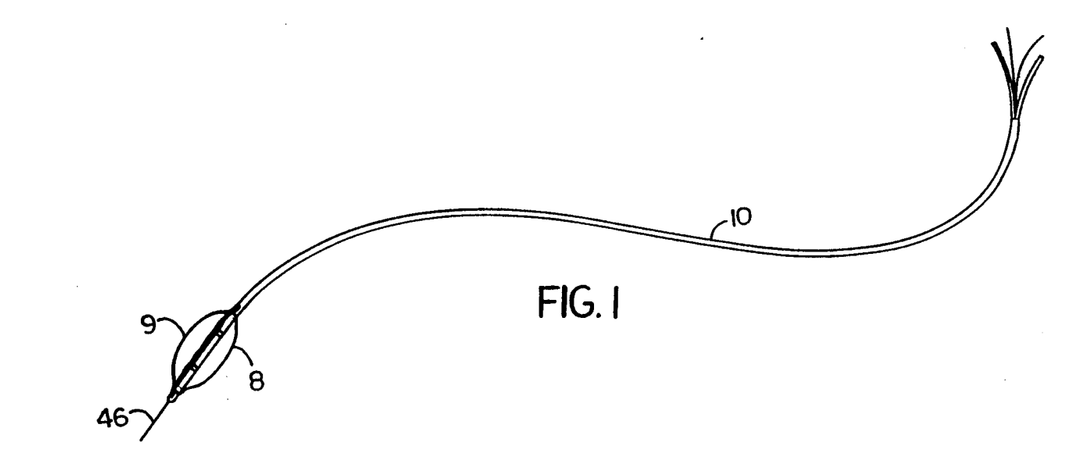
FIG. 1 is a drawing of a balloon catheter according to the invention.
Figure 1A:
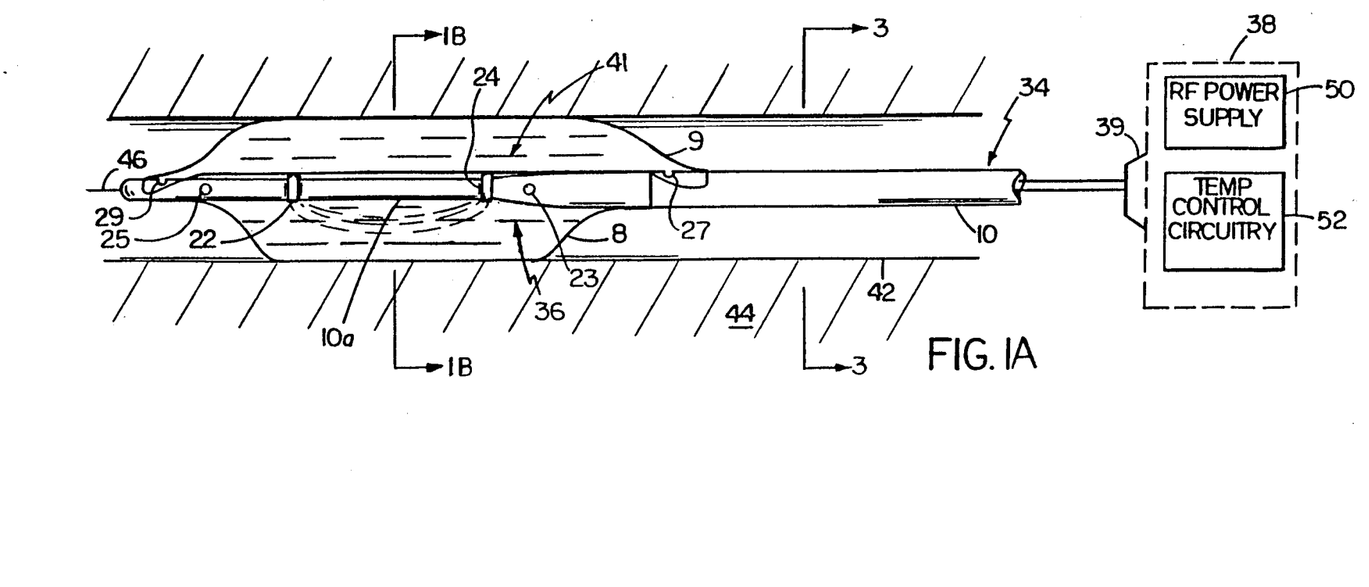
FIG. 1A is a detailed drawing of the balloon portion of the balloon catheter of FIG. 1, showing the balloons in an inflated condition.
Figure 1B:
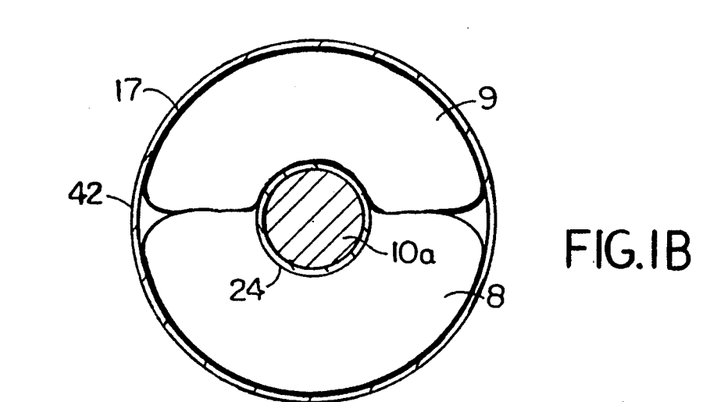
FIG. 1B is a cross-sectional view of the balloon catheter of FIG. 1A, taken along line 1B—1B in FIG. 1A.
Figure 1C:
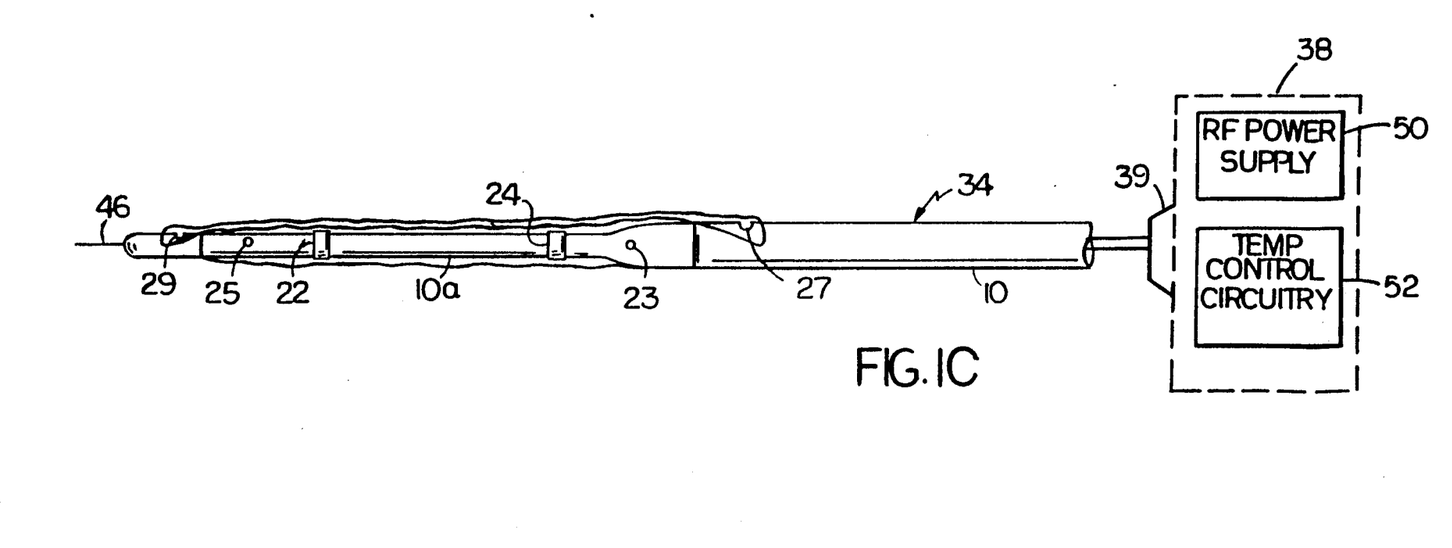
FIG. 1C is a detailed drawing of the balloon portion of the balloon catheter of FIG. 1, showing the balloons in a deflated condition.

In the embodiment of FIGS. 1 through 1C, balloon catheter 34 comprises a nylon catheter shaft 10 and at least two polyethylene terephthalate (PET) balloons 8 and 9. Catheter shaft 10 passes through the length of balloon 8. The proximal and distal ends of balloon 9 are tacked onto catheter shaft 10 at locations adjacent the proximal and distal ends of balloon 8. Catheter shaft 10 includes lumens 23 and 25 within balloon 8 through which fluid enters and exits balloon 8, and lumens 27 and 29 through which fluid enters and exits balloon 9. Balloon 9 may be filled with a gas rather than a liquid, in which case catheter shaft 10 need include only a single lumen for balloon 9.

The fully extended diameter of each of the balloons 8 and 9, when inflated, ranges from 2 millimeters for coronary vascular procedures, to 20 or 35 millimeters for hyperthermia treatment of the prostate, esophagus or colon. The combined volume of the balloons ranges from $\frac{1}{8}$ cc for the smallest balloons to 100 cc for the largest balloons. The wall thickness of the balloons 8 and 9 is about 0.001 inch. In some applications, e.g. where the catheter 34 is being used in a blood vessel, a guidewire 46, which can extend past the distal end of the catheter, may be used to guide the catheter through the vascular system or other luminal structures. The exteriors of the balloons are coated with a non-stick coating having a low coefficient or friction, such as silicone or polysiloxane. The nonheated balloon may be covered with a coat of heat-insulating material or silver heat-reflective material 17 as shown in FIG. 1A, thereby enhancing the temperature difference between the heated balloon and the unheated balloon.

Balloon 8 is fillable with an electrically conductive fluid 36 such as normal saline (0.9 percent NaCl in water), a conductive radiopaque fluid, or a mixture of saline solution and a radiopaque fluid. The other balloon 9 is fillable with fluid 41, including carbon dioxide or air for some applications. A gas will not tend to absorb as much heat from balloon 8 as would a liquid, but for some applications the length of time during which heating occurs is short enough that a liquid will suffice.

In an alternative construction of the embodiment shown in FIGS. 1 and 1A, balloons 8 and 9 may be replaced by a single, multi-segmented balloon. Catheter shaft 10 passes through the length of one of the segments. The other segment connects with catheter shaft 10 at the locations of lumens 27 and 29.

Electrical contacts 22 and 24 are exposed to the fluid 36 inside of one of the balloons 8, but are not exposed to the fluid inside of the other balloon 9. The electrical contacts 22 and 24 are annular in shape. The electrical contacts 22 and 24 have internal diameters matching the portion of the catheter shaft 10 that they surround and are bonded directly to the catheter shaft. The spacing between the electrical contacts 22 and 24 is approximately half the length of the balloons, and the spacing from the respective ends of the balloons is approximately one fourth the length of the balloons, so that balloon 8 will heat evenly. While the dimensions of the contacts vary according to the nature of the medical procedure to be performed, in this embodiment it is preferable that the contacts be in the form of annular thin-wall bands having their axial length and diameter about equal. For the range of uses contemplated for this embodiment, the inner diameter of the smallest contact is about 0.050 inch, and the inner diameter of the largest contact is about 0.120 inch. The contacts have a radial thickness of approximately 0.002 inch, and therefore present a low profile. The contacts can be made of any conductive material that is compatible with the conductive solution and the conditions of use, but are preferably of a radiopaque metal such as platinum or tantalum, so that they may serve as radiopaque markers during placement of the catheter. Contacts 22 and 24 are preferably coated with tin, so that they may be soldered by means of tin solder to (34 gauge, multi-filament, copper wires 20 and 18 respectively), that extend through the length of the catheter shaft and connect with the contacts at locations immediately beneath the contacts. These wires, which are TEFLON-insulated, and have outer diameters of 0.012 inch, connect contacts 22 and 24, respectively, to opposite poles of current-controlled (constant current) radio-frequency power supply 50. Wires 20 and 18 are enclosed within catheter shaft 10 along its length.

RF power supply 50 preferably operates at 650 kilohertz, but can be at any frequency within the range of about 100 kilohertz to 1 megahertz. It is important to use radio frequency power rather than direct or low frequency current, or microwave power, because the risk of physiological response or electrocution response is reduced at RF frequencies about 100 kHz kilohertz as compared with d.c. or low frequencies, and because microwave power would lead to radiative losses in wires within the catheter shaft, that can result, e.g., in unwanted heating of catheter shaft 10. Microwaves would also tend to interfere with the operation of the thermistor even after the microwave power has been turned off. The fluid 36, while selected to have resistive losses, has an electrical impedance low enough that it will conduct the current supplied by RF power supply 50 at voltages of about 100 volts or lower. For example, if the current I is set at 1 amp, and the impedance R between the electrodes, through the fluid is 100 ohms, the voltage V will be 100 volts according to $V=IR$, and the power P dissipated into the fluid will be 100 watts, according to $P — I^2R$. In general, where two electrodes are employed, the impedance between the electrodes will be less than 1000 ohms, preferably in the range of 50 to 500 ohms, and in the present embodiment most preferably at about 100 ohms. In all events the shape of balloon 8 and the construction and spacing of the electrical contacts are preselected so that the electrical current is substantially confined to the interior of balloon 8. The fluid 36 within balloon 8 may be black or dark, so that in addition to the fluid being heated by resistive conductive of RF electric current, the fluid thermally absorbs the RF radiation from the electrodes. A black or dark fluid 36 can therefore heat up more efficiently than a clear fluid or a white fluid.

Catheter 34 plugs into RF power supply and temperature control circuitry 38 by means of a plug 39, that is keyed with respect to the particular size of balloon catheter it is associated with, to cause the power supply to operate at a maximum current of 1/10, $\frac{1}{4}$, $\frac{1}{2}$, or 1 amp. Plug 39 has seven pins, three of which are needed to operate the catheter. During manufacture, a jumper connection is made within plug 39 between a selected two of the remaining four pins. The jumper connection indicates how much current, at maximum, the RF power supply 50 should produce, depending upon which pins the jumper connection connects. Thus, the user need only select the appropriate catheter 34, and need not be concerned about selecting the appropriate maximum current.

Figure 2:
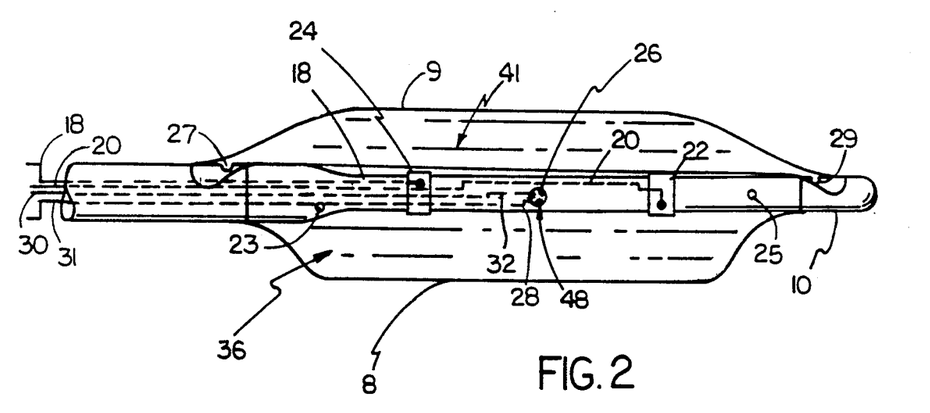
FIG. 2 is a detailed drawing of the balloon portion of the balloon catheter shown in FIG. 1, according to an embodiment of the invention in which a temperature sensing device is mounted inside the balloon.

Referring to FIG. 2, in one embodiment of the invention, a bead thermistor 26, 0.014 inch in diameter and 0.020 inch long, is mounted directly upon catheter shaft 10 between electrodes 22 and 24, in contact with the fluid 36 inside of balloon 8. Stainless steel thermistor leads 28 and 32 connect thermistor 26 with 34-gauge, multi-filament, TEFLON-coated, copper wires 31 and 30 respectively. Wires 31 and 30, which have an outer diameter 0.012 inch, are soldered to the stainless steel thermistor leads 28 and 32, and connect thermistor leads 28 and 32 with RF power supply and temperature control circuitry 38 via the pins of the plug. Thermistor 26 fits snugly on top of an opening 48 in the wall of catheter shaft 10 midway between electrodes 22 and 24. Thermistor leads 28 and 32 and wires 31 and 30 are enclosed within catheter shaft 10, and thermistor leads 28 and 32 connect with thermistor 26 through opening 48. An insulating coating of epoxy or urethane seals thermistor 26 on top of opening 48. Electrodes 22 and 24 are soldered to 34-gauge, multi-filament, copper wires 20 and 18, respectively. These wires, which are TEFLON-insulated, and have outer diameters of 0.012 inch, connect contacts 22 and 24, respectfully to opposite poles of current-controlled (constant current) radio-frequency power supply 50. Wires 20 and 18 are enclosed within catheter shaft 10 along its length, and connect with the contacts at locations immediately beneath the contacts.

Figure 3:
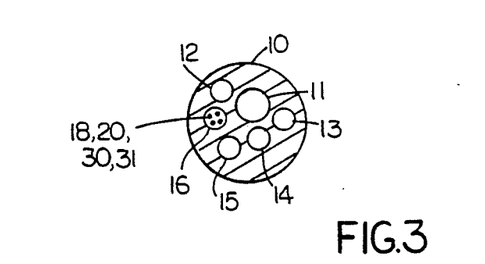
FIG. 3 is a cross-sectional view of the catheter shaft of the balloon catheter shown in FIG. 1, taken along line 3—3 in FIG. 1.

Referring to FIG. 3, catheter shaft 10 has six lumens 11, 12, 13, 14, 15, and 16. Lumen 11 extends from the proximal end of catheter shaft 10 to distal end, and provide a conduit for guidewire 46. Lumens 12 and 13 extend from the proximal end of catheter shaft 10 to a pair of outlets in the inside of balloon 8. Lumen 12 provides a conduit for inflating balloon 8 with fluid 36, and lumen 13 provides a conduit for fluid exiting balloon 8. Likewise, lumen 14 provides a conduit for inflating balloon 9, and lumen 15 provides a conduit for fluid 36 exiting balloon 9. Alternatively, if there are three balloons mounted on catheter shaft 10, the two unheated balloons may be interconnected by a lumen, and a single lumen can be used to inflate one of the interconnected balloons and another single lumen can be used to allow fluid to exit through the other balloon. Lumen 16 extends from the proximal end of catheter shaft 10 to the inside of balloon 8. Lumen 16 provides a conduit for wires 18 and 20, and for wires 31 and 30 which connect with thermistor leads 28 and 32 within lumen 16.

Figure 4:
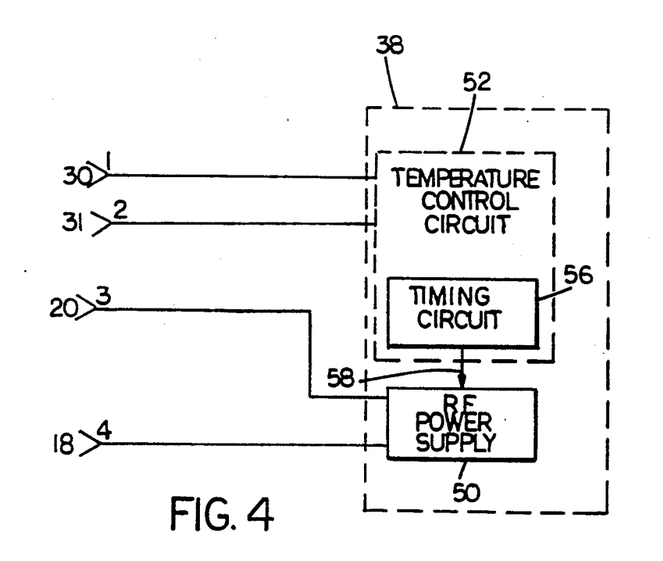
FIG. 4 is a block diagram of the RF power supply and temperature control circuitry according to the embodiment of the invention of FIG. 2.

Referring to FIG. 4, RF power supply and temperature control circuitry 38 consists of RF power supply 50, temperature control circuit 52. Wires 18 and 20 connect electrodes 24 and 22, respectively, with RF power supply 50, and wires 31 and 30 connect thermistor leads 28 and 32 with temperature control circuit 52. Timing circuit 56 of temperature control circuit 52 toggles hold/NOT sample line 58, causing RF power supply 50 to turn on and off for purposes of power application and temperature sensing respectively. The temperature sensing period is 1 percent of the 60 hertz cycle. During the temperature sensing period, temperature control circuit 52 determines how much power, at maximum, RF power supply 50 should supply during the next power application period. By thus time-sharing between temperature sensing and application of current to the electrodes, the temperature control circuitry eliminates the possibility that thermistor 26 will pick up RF noise from the electrodes 22 and 24.

Figure 5:
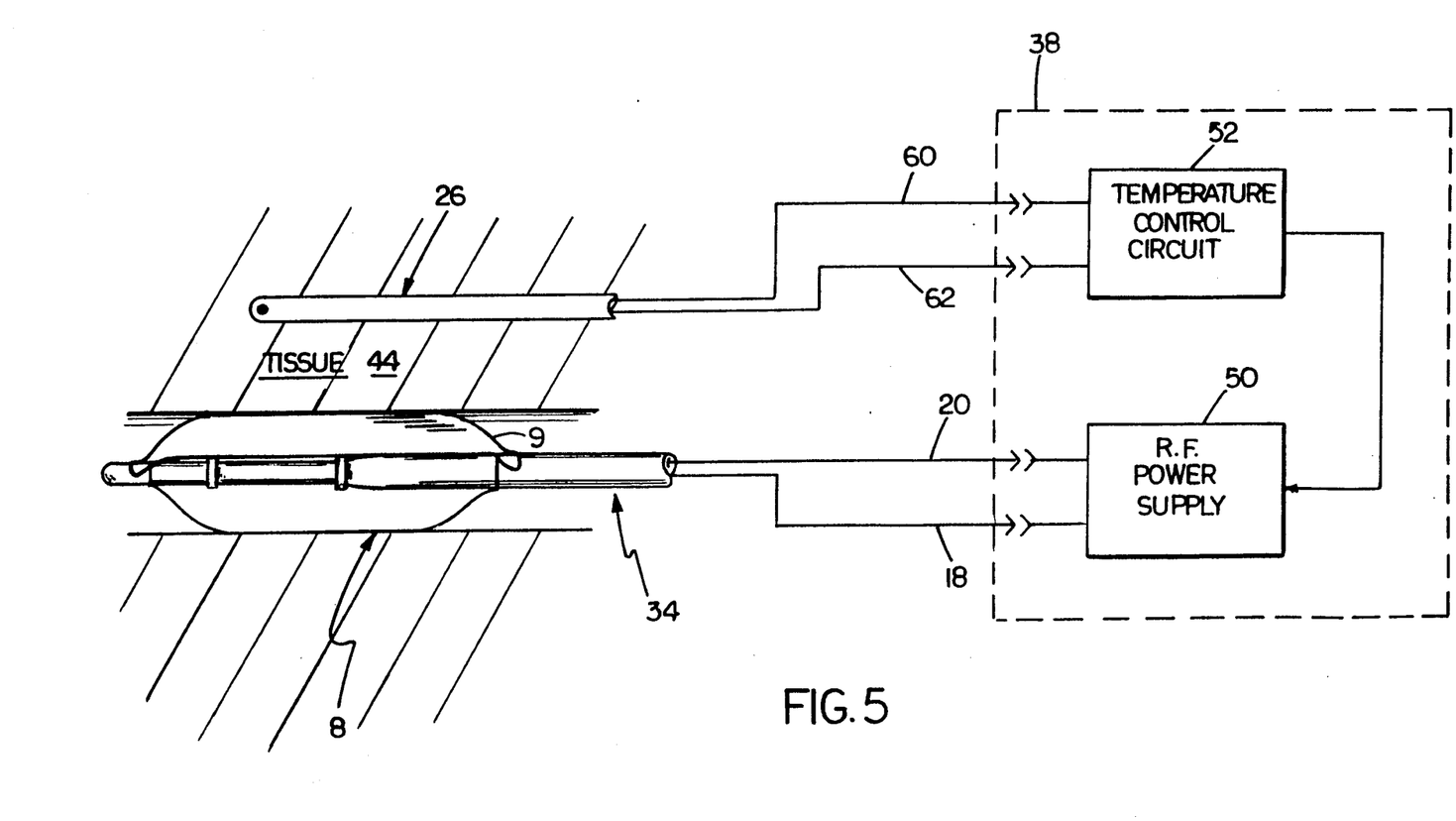
FIG. 5 is a block diagram of the RF power supply and temperature control circuitry according to an embodiment of the invention in which a temperature sensor is placed in direct contact with the tissue surrounding the balloon.

Referring to FIG. 5, another embodiment of the invention is shown in which temperature sensor 26 is placed in direct contact with tissue 44, outside of balloon catheter 34. Wires 60 and 62 connect temperature sensor 26 with temperature control circuit 52, and wires 20 and 18 connect electrodes 22 and 24 respectively with RF power supply 50. Temperature control circuit 52 regulates RF power supply 50 in response to the input from temperature sensor 26.

Figures 7, 8:
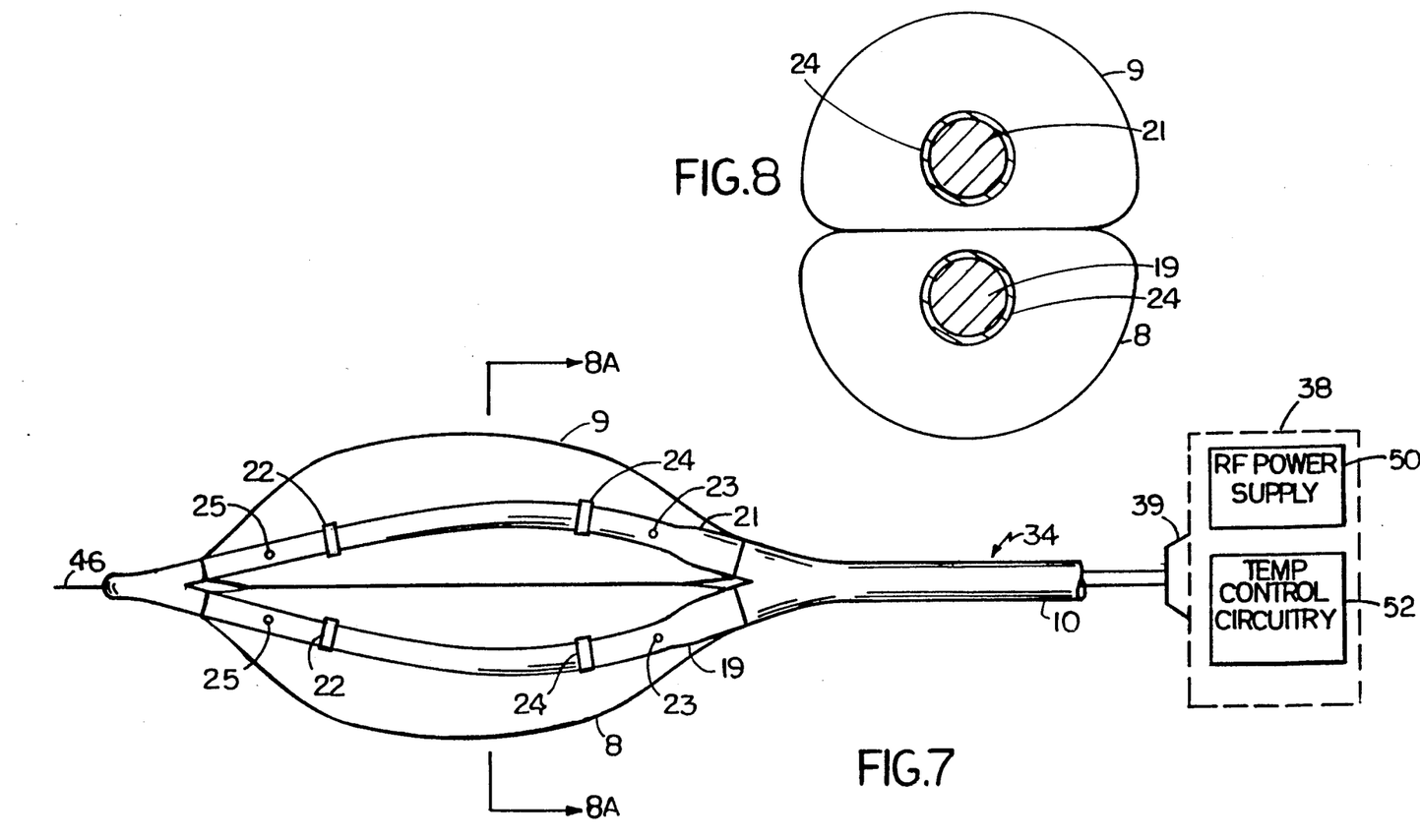
FIG. 7 is a drawing of a balloon catheter according to an embodiment of the invention in which multiple balloons are heated differentially.
FIG. 8 is a cross-sectional view of the balloon catheter of FIG. 7, taken along line 8—8 in FIG. 7.

FIGS. 7 and 8 illustrate another embodiment of the invention, in which catheter 10 branches into two portions 19 and 21 that pass through balloons 8 and 9 respectively. Catheter portions 19 and 21 merge together at a point distal to balloons 8 and 9. A pair of electrical contacts is located within each balloon. Each of catheter portions 19 and 21 includes a lumen for electrical wires and one or two lumens for fluid flow. The lumens for the electrical wires branch off of a single common lumen within catheter 10, but the lumens for fluid flow may be separate throughout the entire length of catheter 10, in order to enable the balloons to be filled with differing fluids or to differing pressures. Instead of the user manipulating the balloons so that a heated balloon faces the lesion, the appropriate balloon can be selected for heating without the need for manipulation of the catheter 10. If more than two balloons are used, several balloons may be heated at the same time, to provide heating in several directions, short of a full circumferential heating. Thus, the ratio of heated balloons to non-heated balloons determines the radius of heating. Moreover, the user may decide not to inflate one or more of the balloons, thereby affecting the radius of heating. Note that the balloons may differ in size.

The embodiment of FIGS. 7 and 8 is useful also for differential heating. For example, one balloon can be heated to 90° C. while another balloon is heated to 60° C. The balloons are filled with fluids having differing saline concentrations and hence having differing resistivities, resulting in differential heating of the balloons. Alternatively, the spacing between electrical contacts 22 and 24 may be greater in one balloon than in the other, resulting in differential heating. If the relative extent of heating of the balloons is known from empirical data, the temperature control circuitry 52 need only monitor the temperature of one of the balloons. Alternatively, differential heating may be achieved by separately measuring the temperature of each balloon. The electrical contacts within balloons 8 and 9 can be connected to a common pair of electrical wires, or to separate pairs of wires, as shown, to enable separate control of the heating of each balloon by separate power supply and temperature control circuits.

Figure 9:
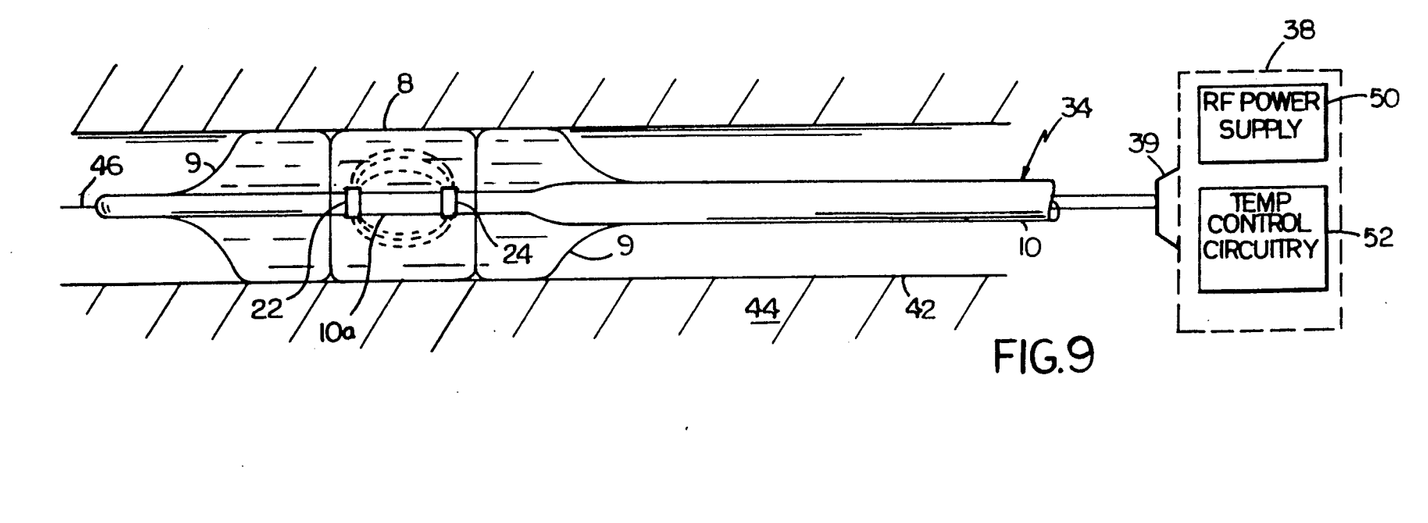
FIG. 9 is a drawing of a balloon catheter according to an embodiment of the invention in which balloons are disposed axially with respect to each other along the catheter shaft.

Referring to FIG. 9, another embodiment of the invention is shown in which three balloons are disposed axially, rather than radially, on catheter shaft 10. Electrical contacts 22 and 24 are exposed to the fluid 36 inside the central balloon 8, but not the fluid inside the two end balloons 9. Thus, the two end balloons will be cool enough that they will not cause blood to coagulate within a blood vessel when the catheter is used in a blood vessel application. The embodiment of FIG. 9 can be modified by placing electrical contacts within each balloon, in order to provide for differential heating and the other advantages of the embodiment of FIGS. 7 and 8.

Figures 10, 10A:
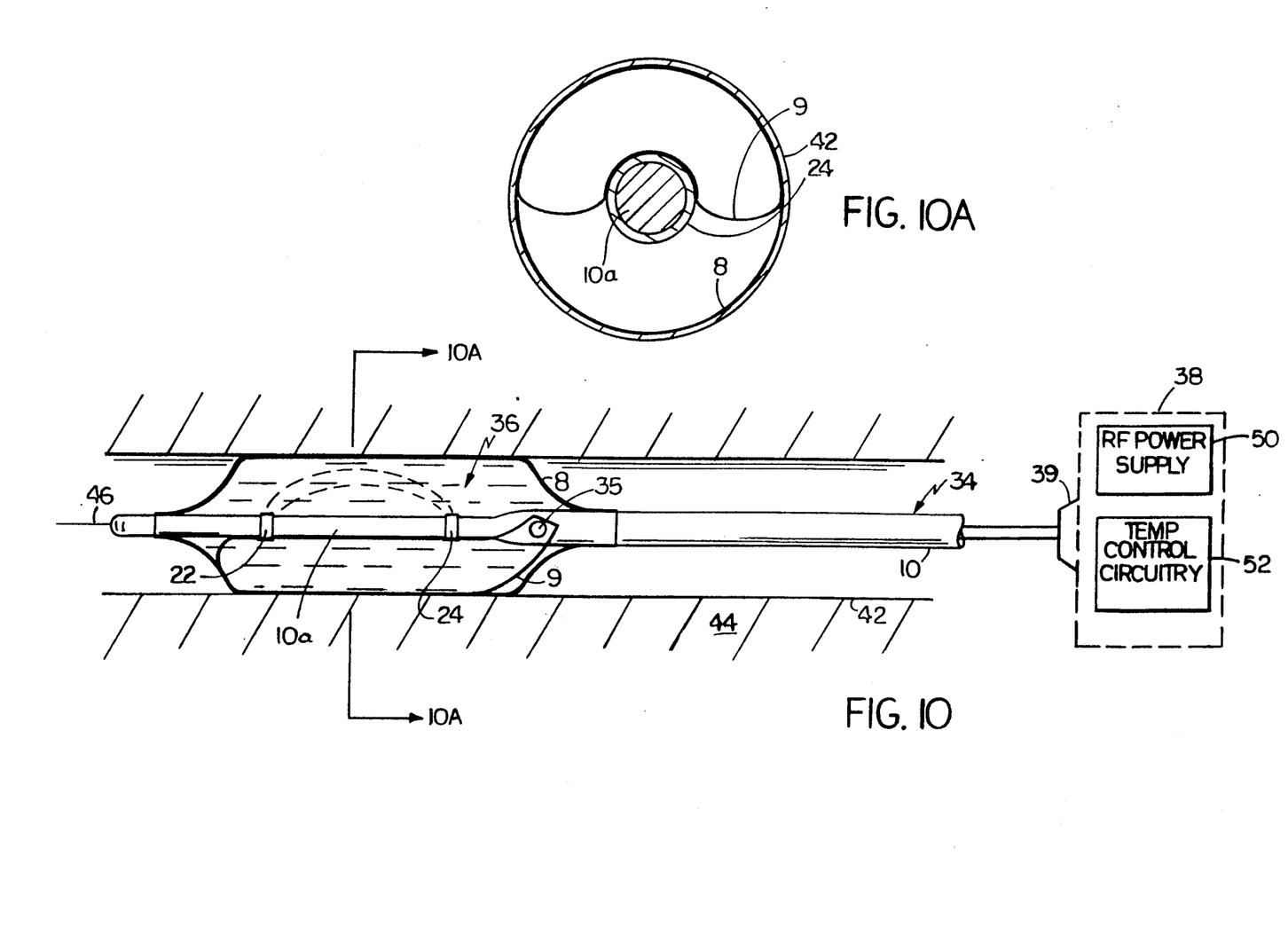
FIG. 10 is a drawing of a balloon catheter according to an embodiment of the invention in which one balloon is disposed within another balloon.
FIG. 10A is a cross-sectional view of the balloon catheter of FIG. 10, taken along line 10A—10A in FIG. 10.

FIGS. 10 and 10A illustrate another embodiment of the invention in which balloon 9 is disposed within balloon 8. Balloon 9 is preferably a latex, distensible balloon and balloon 8 is preferably nondistensible. Catheter shaft 10 passes through the length of balloon 8, but not through balloon 9. Balloon 9 is attached to catheter shaft 10 within balloon 8 at the location of a lumen 35 in catheter shaft 10 through which balloon 9 is inflated with fluid. It does not matter whether electrodes 22 and 24 contact the surface of balloon 9, because the fluid within balloon 9 is thermally insulating, preferably a gas.

Figure 11:
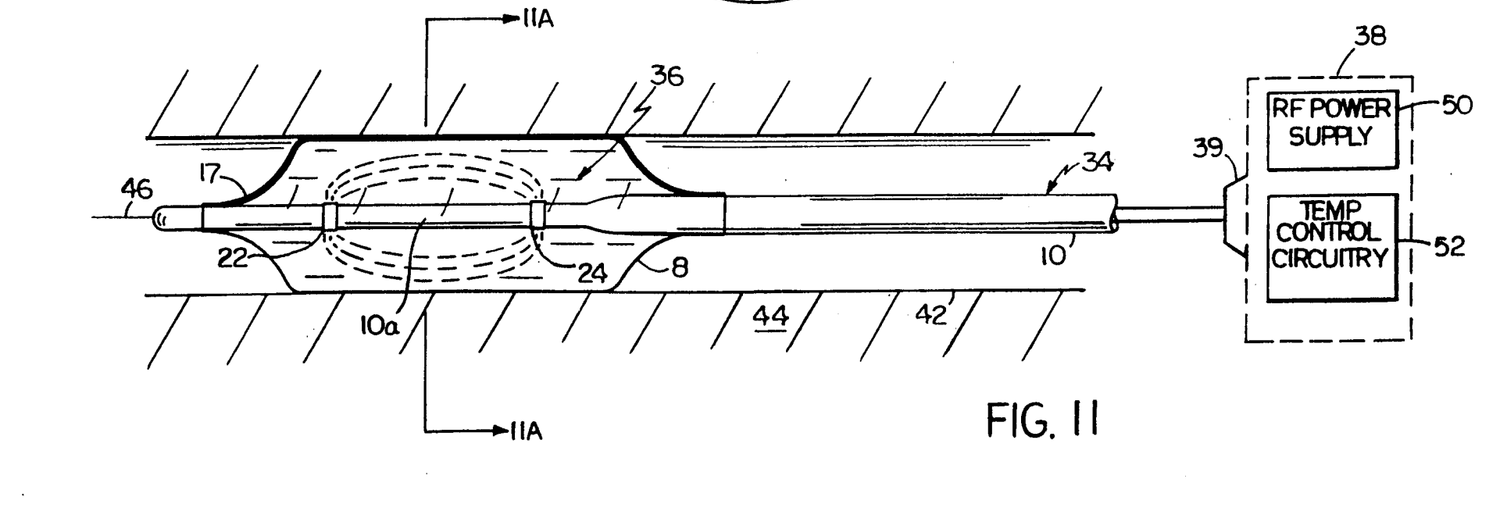
FIG. 11 is a drawing of a balloon catheter according to an embodiment of the invention in which a single balloon is partially coated with a heat-insulating or heat-reflective material.
Figure 11A:
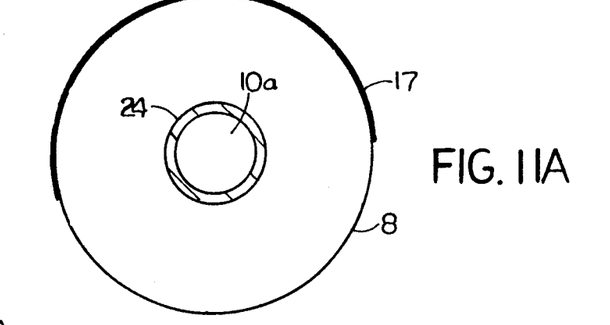
FIG. 11A is a cross-sectional view of the balloon catheter of FIG. 11, taken along line 11A—11A in FIG. 11.

Referring to FIGS. 11 and 11A, another embodiment of the invention is shown in which a single balloon 8 is mounted on the catheter shaft 10. A coat of heat-insulating material or silver heat-reflective material 17 is applied to the parts of the balloon surface that do not face the lesion. The parts of the balloon surface that face the lesion are left uncovered, so that heat will tend to flow in the direction of the lesion. Alternatively, if the catheter is to be used in blood vessels, the axial ends of the balloon 8 may be covered with the heat-insulating or heat-reflective material 17 so as to avoid heating up blood fluid in the blood vessel.

Figure 12:
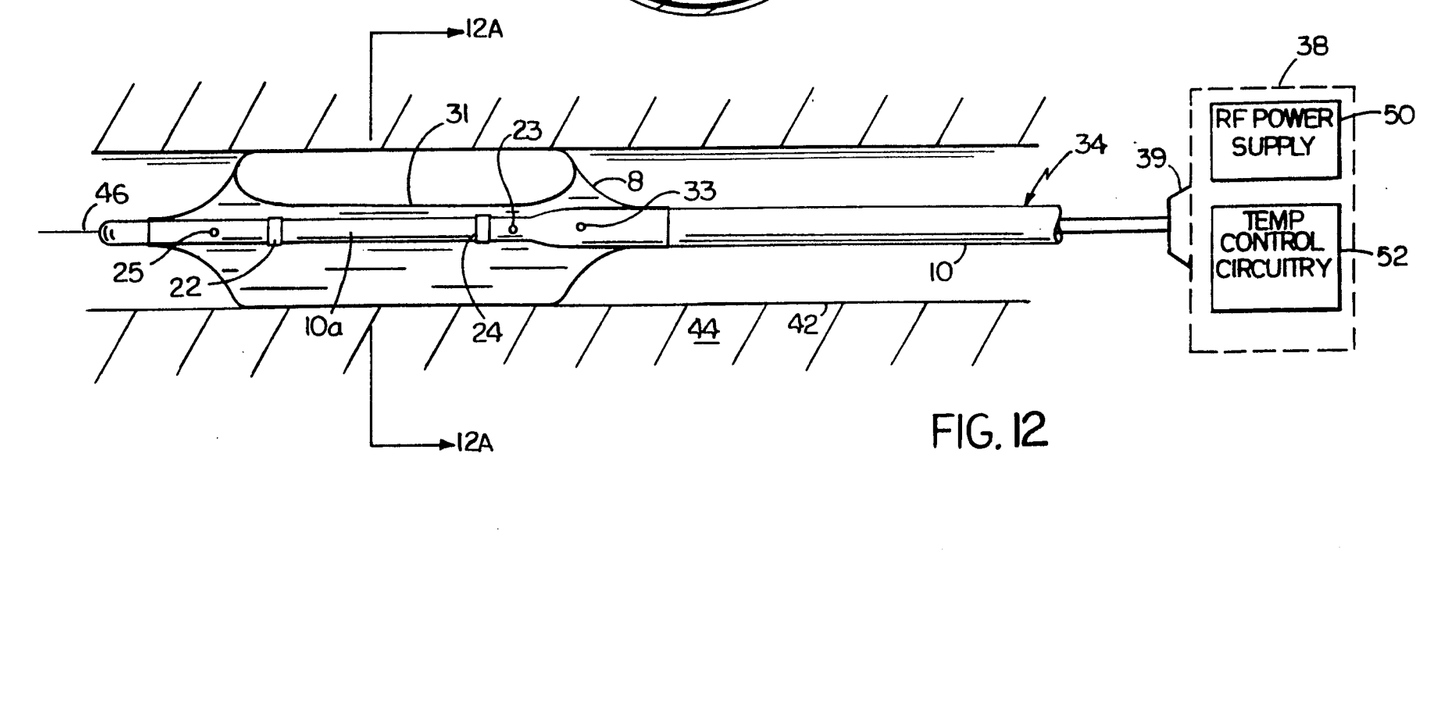
FIG. 12 is a drawing of an embodiment of the invention in which a single balloon contains an electrically conductive fluid and a bubble of gas.
Figure 12A:
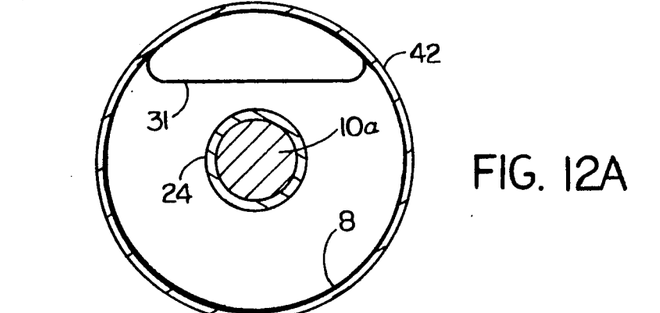
FIG. 12A is a cross-sectional view of the balloon catheter of FIG. 12, taken along line 12A—12A in FIG. 12.

FIGS. 12 and 12A illustrate yet another embodiment of the invention, in which a single balloon 8 is filled with an electrically conductive fluid 36 and with a bubble 31 of air or another suitable gas. Catheter shaft 10 includes a lumen 33 through which the air enters balloon 8, in addition to lumens 23 and 25, through which the electrically conductive fluid enters and exits balloon 8. This embodiment of the invention is useful in applications in which it is possible to position the patient in a manner such that the tissue to be heated is located beneath balloon 8. Gravity causes the air bubble to rise to the upper portion of balloon 8, thereby insulating tissue located above balloon 8 from heat.

Figure 6:
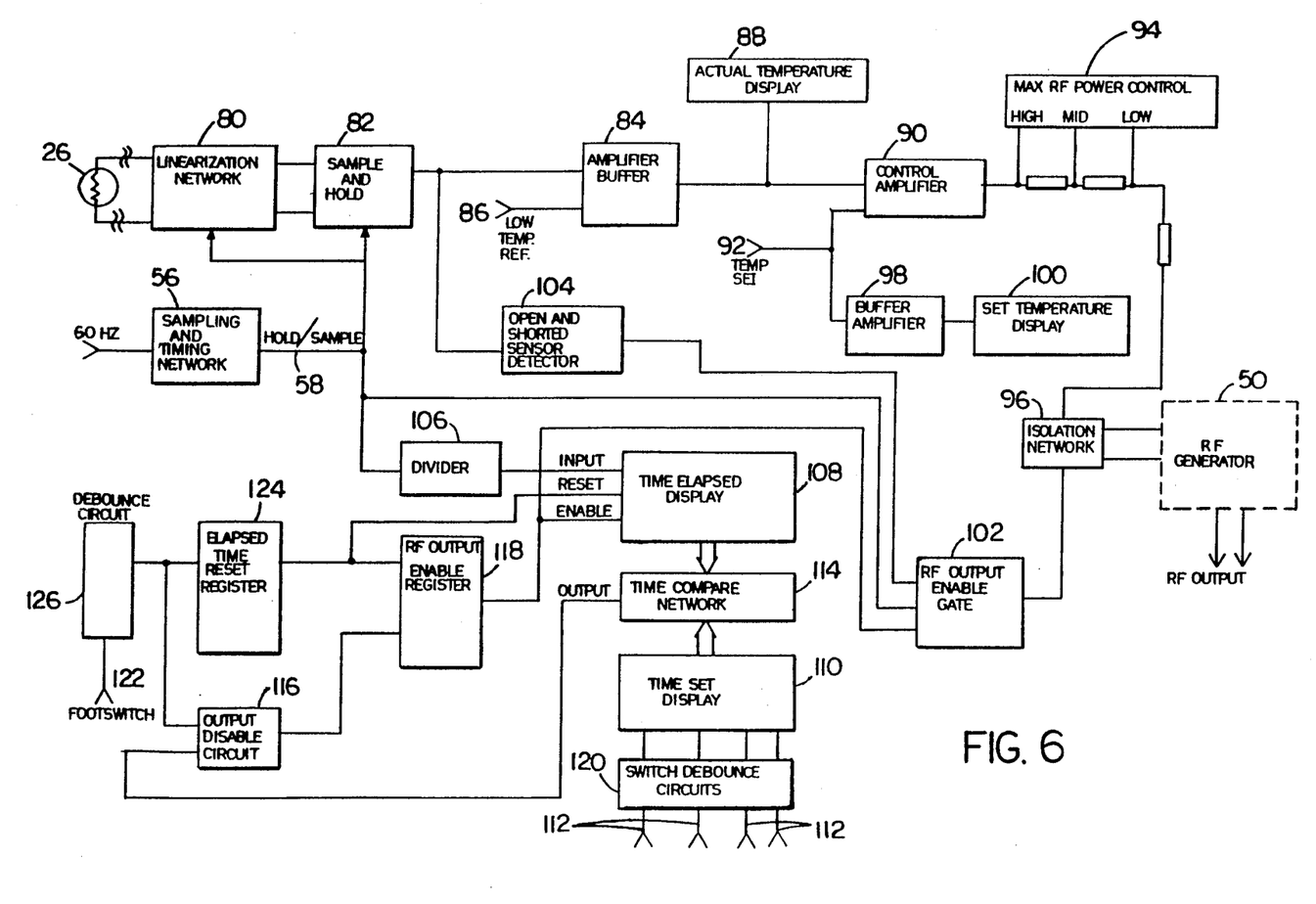
FIG. 6 is a detailed block diagram of the temperature control circuit shown in FIGS. 4 and 5.

Referring to FIG. 6, in temperature control circuit 52, linearization network 80 linearizes the input signal from temperature sensor 26 and delivers the linearized signal to sample and hold register 82. The signal is delivered to amplifier buffer 84 having low-temperature reference 86. Actual temperature display circuit 88 displays the output of amplifier buffer 84. Control amplifier 90 compares the output of amplifier buffer 84 with a temperature set voltage 92 that is set by the user. The maximum RF power control circuit 94 receives the output of control amplifier 90 and determines the level of RF power, at maximum, that the RF power supply 50 should produce. The signal from the maximum RF power control circuit 94 is received by isolation network 96, which interfaces with RF power supply 50. The temperature set voltage 92 is received by buffer amplifier 98 and displayed by set temperature display 100.

Timing circuit 56 toggles hold/NOT sample line 58 at 60 hertz, so that hold/NOT sample line 58 is low during 1 percent of the cycle and high during the other 99 percent of the cycle. Hold/NOT sample line 58 is low when signals from temperature sensor 26 are being sampled and high when signals from temperature sensor 26 are not being sampled. Hold/NOT sample line 58 is received by RF output enable gate 102. The output of sample and hold register 82 is processed by open and short sensor detector 104 to determine whether a sensor malfunction, such as a shorted or open sensor, has occurred. The output of open and shorted sensor detector 104 is received by RF output enable gate 102. RF output enable gate 102 delivers a signal to isolation network 96, which turns off RF power supply 50 when there has been a sensor malfunction or when signals from temperature sensor 26 are being sampled.

Divider 106 receives hold/NOT sample line 58 and delivers its output to time elapsed display 108. Time set display 110 displays the time indicated by time set switches 112, which are set by the user. Time compare network 114 compares the elapsed time with the time set by the user, and delivers an output signal to output disable circuit 116. The output of output disable circuit 116, which is active only when the elapsed time is less than the time set by the user, is delivered to RF output enable register 118. RF output enable register 118 in turn delivers the signal to the enable input to time elapsed display 108, and also to RF output enable gate 102, so that RF power supply 50 may be turned off when the time set by the user has elapsed. Switch debounce circuits 120 are provided for time set switches 112.

The user must depress footswitch 122 in order for RF power supply 50 to operate. While footswitch 122 is activated, and while the elapsed time is less than the time set by the user, output disable circuit 116 delivers a signal to RF output enable register 118, which in turn delivers the signal to the enable input of time elapsed display 108, and also to RF output enable gate 102 so that rf power supply 50 may be turned on. Deactivation of footswitch 122 causes a signal to pass through elapsed time reset register 124, in order to reset time elapsed display 108 and in order to reset RF output enable register 118. The resetting of RF output enable register 118 causes RF output enable gate 102 to turn off RF power supply 50. Debounce circuit 126 is provided for footswitch 122.

OPERATION

Referring to FIG. 1, balloon catheter 34 may be used as a heat source for treatment of lesions located eccentrically on ducts 42 in the body, including treatment of tumors of the esophagus. The user first preselects the desired therapeutic temperature (temperature set voltage 92, FIG. 6), and sets the length of time for which balloon 8 is to be heated (time set switches 112, FIG. 6). The balloon catheter 34 is then inserted into the esophagus or other vessel or duct in the body. If the balloons 8 and 9 contain conductive radiopaque fluid, the location of the balloons can be monitored by means of fluoroscopy. The user positions the catheter 34 so that balloon 8 is facing towards the lesion and balloon 9 is facing away from the lesion. Balloons 8 and 9 are inflated through lumens 12 and 14 with either saline, a conductive radiopaque fluid, or a mixture of saline and a radiopaque fluid, to a pressure of at least 2 atmospheres. The user may inflate one of the balloons 8 or 9 fully and the other balloon only partially, preferably with a non-compressible fluid. The partially inflated balloon tends to wrap around the fully inflated balloon, so that only a relatively small portion of the surface of the fully inflated balloon remains exposed.

The balloons remain inflated, the entire circumference of the duct being engaged by the walls of the balloons, while the user depresses footswitch 122 (FIG. 6) to initiate the bi-polar heating between the electrodes 22 and 24. Heat is dissipated into the fluid within balloon 8 according to the formula $P = I^2 R$ where P is the power that is dissipated into the fluid, I is the current that is passed through the electrodes, and R is the resistance of the fluid. The heat from the fluid is conducted across the wall of balloon 8 into the surrounding tissue 44 in the direction of the lesion, but not in the direction away from the lesion, so that healthy tissue is not damaged. If the lesion is located at a stenosis and the electrodes of the heated balloon are centered at the location of the stenosis, the heated balloon will tend to be hottest at the narrowed portion in the vicinity of the electrodes, because the electrical current density will be greatest at that location and fluid circulation within the balloon will be restricted. The fluid will heat to the temperature set by the user, which may be in the range of 45° Celsius to 80° Celsius. Heating will continue until the time set by the user has elapsed, or until the user deactivates footswitch 122. Cooling fluid may be circulated through the unheated balloon 9 through lumens 14 and 15 while balloon 8 is being heated. Cooling fluid may be circulated through both balloons 8 and 9 after heating as well, although the balloons tend to cool down fairly quickly by thermal transfer of heat into the surrounding tissue 44.

Embodiments of the invention in which each of multiple balloons contains electrodes are useful in applications in which directional heating is not required. Either one or more than one of the balloons can be inflated, so as to provide for the appropriate amount of compression of the lesion. If necessary, several balloons having differing volumes can be used, thereby providing a greater number of possible total volumes that the non-distensible balloons can occupy, and hence providing a greater variability in the amount of compression of the lesion. By regulating the amount of compression of the lesion, the user can control the effectiveness of transfer of heat to the lesion, because the tissue loses its ability to act as a heat sink when the tissue is compressed, especially if there is blood ordinarily flowing through the tissue. RF current can be applied to each pair of electrodes in each of the balloons, because conduction of RF current will occur only in the balloons that contain fluid.

Catheters according to the invention can be used in nonvascular applications such as hyperthermia treatment of benign or malignant tumors. Hyperthermic effects begin at about 44° Celsius. Heat from balloon 8 destroys the undesired cells, which are eventually absorbed into the patient's body. When a catheter according to the invention is used in such nonvascular applications, the balloons 8 and 9 may be large enough that no temperature sensing device is needed, and the fluid 36 can be left to boil at the electrodes without the buildup of excessive pressure within the balloon. The fluid will begin to boil locally in about 5 seconds if the balloon has a diameter of 4 millimeters.

The embodiments of the invention that provide multiple balloons heated to differing temperatures are especially useful in treatment of enlarged prostate glands. The enlarged prostate surrounds the urethra but is eccentric with respect to the urethra. The user inserts the catheter into the urethra and positions the balloons in a manner such that a hotter balloon will face the bulk of the mass of the prostate and a balloon that is heated less will face the opposite direction. It is also possible to use smaller catheters according to the invention for blood vessel applications, such as treatment of eccentrically located plaque in blood vessels.

Other embodiments are within the following claims.

We claim:

1. A catheter device for heating tissue, comprising
a longitudinally extending catheter shaft constructed for insertion into a patient's body, said catheter shaft defining at least one lumen for fluid flow through said shaft,
at least a first liquid-expandable chamber mounted on said catheter shaft, said chamber defined at least in part by a flexible wall that engages body tissue, said chamber being associated with said lumen for liquid communication with a liquid source outside the body, said chamber being fillable thereby with said liquid after placement in the body,
a heating device, in contact with said liquid within said chamber when said chamber is expanded, for heating said liquid, so that heat of a controlled temperature can be transmitted from said liquid to surrounding tissue by thermal conduction through said wall of said first chamber, and
means for selectively directing said heat transmission to a selected portion of tissue engaged by said catheter device, said means being interposed between said heated liquid in said chamber and another portion of said tissue to inhibit thermal conduction of heat from said heated liquid to said other portion of said tissue while heat is transmitted from said heated liquid through the wall of said chamber to said selected portion of tissue.

2. The device of claim 1 wherein said heating device comprises a plurality of spaced electrical contacts enclosed within said first chamber and a corresponding plurality of conductors for connecting said electrical contacts to a power supply for supplying a radio frequency electrical potential to said contacts, said heating device being adapted to operate with liquid within said first chamber that is electrically conductive and preselected to produce resistive heating,
said contacts being exposed to the liquid within said first chamber when said first chamber is expanded so that said radio frequency electrical potential can cause current to flow through liquid between said contacts,
said first chamber being sufficiently spaced apart from said contacts when said first chamber is expanded to ensure that said current is substantially confined to liquid within said first chamber,
said liquid being heatable on the basis of $I^2R$ losses of said radio frequency electric current flowing between said electrical contacts.

3. The device of claim 1 or 2 wherein said means for selectively directing the heat transmission comprises at least a second chamber fillable with fluid having a different thermal effect than said liquid of said first chamber, said second chamber being mounted adjacent to said first chamber in a position to engage at least part of the tissue surrounding said catheter device.

4. The device of claim 3 wherein said fluid of said second chamber differs from said liquid of said first chamber.

5. The device of claim 3 wherein said fluid of said second chamber is the same as said liquid of said first chamber.

6. The device of claim 3 wherein said second chamber is fillable with liquid, further comprising an auxiliary heating device for heating said liquid within said second chamber instead of said liquid within said first chamber, so that said heat transmission can be selectively directed by selecting one of said first and second chambers for heating.

7. The device of claim 3 wherein said second chamber is fillable with liquid, further comprising an auxiliary heating device for heating said liquid within said second chamber to a controlled temperature that differs from said controlled temperature of said liquid within said first chamber.

8. The device of claim 3 wherein said chambers are disposed at differing positions radially upon said catheter device.

9. The device of claim 3 wherein said chambers are disposed at differing positions longitudinally along said catheter shaft.

10. The device of claim 9 wherein there are at least three chambers, one of said chambers being disposed distal to said first chamber, and one of said chambers being disposed proximal to said first chamber along said catheter shaft, said distal and proximal chambers each being fillable with fluid having a different thermal effect than said liquid of said first chamber.

11. The device of claim 1 or 2 wherein said means for selectively directing the heat transmission comprises at least a second chamber mounted within said first chamber, said second chamber being fillable with fluid having a different thermal effect than said liquid of said first chamber.

12. The device of claim 1 or 2 wherein said means for selectively directing the heat transmission comprises at least a second chamber enveloping said first chamber, said second chamber being fillable with fluid having a different thermal effect than said liquid of said first chamber.

13. The device of claim 1 or 2 wherein said means for selectively directing the heat transmission comprises a bubble of gas located within said chamber when said chamber is expanded to thermally insulate tussue located above said chamber from said heat of said liquid within said chamber.

14. The device of claim 1 or 2 wherein said means for selectively directing the heat transmission comprises a heat transmission blocker in contact with a wall of said first chamber.

15. The device of claim 14 wherein said heat transmission blocker comprises a heat-insulating material applied to a portion of said wall of said first chamber to make said portion of said first chamber wall resistant to heat transmission.

16. The device of claim 14 wherein said heat transmission blocker comprises a heat-reflective surface applied to a portion of said wall of said first chamber to make said portion of said first chamber wall resistant to heat transmission.

17. The device of claim 14 wherein
said means for selectively directing the heat transmission further comprises at least a second chamber mounted adjacent to said first chamber, said second chamber being fillable with fluid having a different thermal effect than said liquid of said first chamber, said second chamber being mounted adjacent to said first chamber in a position to engage at least part of the tissue surrounding the catheter device, and said heat blocker is in contact with a tissue conformable wall of said second chamber.

18. The device of claim 17 wherein said heat blocker further comprises a heat-insulating material applied to the wall of said second chamber to make said second chamber wall resistant to heat transmission.

19. The device of claim 17 wherein said heat blocker comprises a heat-reflective surface applied to the wall of said second chamber to make said second chamber wall resistant to heat transmission.

20. The device of claim 3 wherein at least one of said chambers of said catheter device is associated with a plurality of lumens of said catheter device, for cooling fluid flow between said chamber and a fluid source outside the body.

21. The device of claim 2 further comprising
   a power supply constructed to operate at a frequency between 100 kHz and 1 MHz and electrically connected to said plurality of conductors,
   means, in contact with said liquid within said chamber when said chamber is expanded, for monitoring the temperature of said liquid, and
   a temperature control circuit for controlling the output of said power supply in response to information received from said temperature monitoring means.

22. A catheter device for heating tissue, comprising
   a longitudinally extending catheter shaft constructed for insertion into a patient's body, said catheter shaft defining at least one lumen for fluid flow through said shaft,
   at least a first liquid-expandable chamber mounted on said catheter shaft, said chamber defined at least in part by a flexible wall that engages body tissue, said chamber being associated with said lumen for liquid communication with a liquid source outside the body, said chamber being fillable thereby with said liquid after placement in the body, said chamber being nondistensible when fully inflated,
   a heating device, in contact with said liquid within said first chamber when said first chamber is expanded, for heating said liquid within said first chamber, so that heat of a controlled temperature can be transmitted from said liquid to surrounding tissue by thermal conduction through said wall of said first chamber, and,
   at least a second chamber fillable with fluid having a different thermal effect than said liquid of said first chamber, said second chamber being mounted adjacent to said first chamber in a position to engage at least part of the tissue surrounding said catheter device to inhibit thermal conduction of heat from said heated liquid within said first chamber to tissue engaged by said second chamber while heat is transmitted from said heat liquid within said first chamber through the wall of said first chamber to tissue engaged by said first chamber, so that heat transmission is selectively directed to a selected portion of tissue engaged by said catheter device,
   said chambers being disposed at differing positions radially upon said catheter device.

23. The device of claim 22 wherein said first and second chambers are sufficiently large to permit said catheter device to be used for treatment of esophageal tissue.

24. The catheter device of claim 22 wherein said first and second chambers are fillable to differing pressures, to cause one of said first and second chambers to wrap around a portion of the other chamber.

25. The catheter device of claim 22 in the form of a urethral catheter constructed and arranged for treatment of prostatic tissue surrounding a urethra,
   said device further comprising an auxiliary heating device for heating said fluid within said second chamber to a controlled temperature that differs from said controlled temperature of said liquid within said first chamber.

26. A catheter device for heating tissue, comprising
   a catheter shaft constructed for insertion into a patient's body, said catheter shaft defining at least one lumen for fluid flow through said shaft,
   at least a first liquid-expandable chamber mounted on said catheter shaft, said chamber defined at least in part by a flexible wall that engages body tissue, said chamber being associated with said lumen for liquid communication with a liquid source outside the body, said chamber being fillable thereby with said liquid after placement in the body, said chamber being nondistensible when fully inflated,
   a heating device, in contact with said liquid within said first chamber when said first chamber is expanded, for heating said liquid, so that heat of a controlled temperature can be transmitted form said liquid to surrounding tissue by thermal conduction through said wall of said first chamber, and
   at least a second chamber fillable with fluid having a different thermal effect than said liquid of said first chamber, said second chamber being mounted adjacent to said first chamber in a position to engage at least part of the tissue surrounding said catheter device to inhibit thermal conduction of heat from said heated liquid within said first chamber to tissue engaged by said second chamber while heat is transmitted from said heated liquid within said first chamber through the wall of said first chamber to tissue engaged by said first chamber, so that heat transmission is selectively directed to a selected portion of tissue engaged by said catheter device,
   said chambers being disposed at differing positions longitudinally along said catheter shaft.

27. The device of claim 26 in the form of a vascular catheter constructed and arranged to treat blood vessel tissue.

28. The device of claim 8, wherein
   said catheter shaft defines a plurality of lumens for fluid flow through said shaft,
   each of said chambers is defined at least in part by a flexible wall that engages body tissue, each of said chambers being associated with at least one said lumens for fluid communication with a fluid source outside the body, said chambers being fillable thereby with said fluid after placement in the body, and
   at least a first of said chambers is fillable with said fluid separately from at least a second of said chambers, so that said plurality of chambers can occupy any of a plurality of possible total volumes,
   whereby, by selecting said total volume of said plurality of chambers, compression of said tissue can be controlled, and hence effectiveness of transfer of heat to said tissue can be controlled.

29. The device of claim 28 wherein said first chamber and said second chamber have substantially similar dimensions.

30. A method of heating tissue from within a duct in a patient's body, comprising the steps of
   inserting into the duct a catheter device comprising at least a first fluid-expandable chamber, said chamber being defined at least in part by a flexible wall that engages body tissue,
   filling said first chamber with liquid through a lumen extending through a catheter shaft on which said chamber is mounted, so that said wall of said first chamber expands to engage surrounding tissue, heating said liquid, so that heat of a controlled temperature is transmitted from said liquid to surrounding tissue by thermal conduction through a wall of said first chamber, and selectively directing said heat transmission to a selected portion surrounding tissue by inhibiting thermal conduction of heat from said heated liquid to another portion of said tissue while heat is transmitted from said heated liquid through the wall of said chamber to said selected portion of said surrounding tissue.

31. The method of claim 30, wherein said liquid within said first chamber is an electrically conductive liquid preselected for resistive heating, a plurality of spaced electrical contacts are enclosed within said first chamber, a corresponding plurality of conductors connect said electrical contacts to a power supply for applying a radio-frequency electrical potential to said contacts, said contacts are exposed to the liquid within said first chamber when said first chamber is expanded so that said radio-frequency electrical potential can cause current to flow through liquid between said contacts, said wall of said first chamber is sufficiently spaced apart from said contacts when said first chamber is expanded to ensure that said current is substantially confined to said liquid within said first chamber, and said step of heating said liquid comprises the step of applying a radio-frequency potential to said electrical contacts, whereby on the basis of $I^2R$ losses of said radio-frequency electric current flow between said electrical contacts, said liquid is heated and said liquid in turn heats surrounding tissue by thermal conduction through a wall of said first chamber.

32. The method of claim 30 or 31 wherein said step of selectively directing said heat transmission comprises the steps of inserting into said body at least one second said chamber adjacent to said first chamber, said second chamber being integrally connected with said first chamber and said catheter shaft, in a position to engage at least part of the tissue surrounding said catheter device, and filling said second chamber with a fluid having a different thermal effect than said liquid of said first chamber.

33. The method of claim 32 further comprising the step of inflating said second chamber to a pressure that differs from a pressure of said first chamber, to cause one of said first and second chambers to wrap around a portion of the other chamber.

34. The method of claim 30 or 31 wherein said step of selectively directing said heat transmission comprises the step of making a portion of said first chamber wall resistant to heat transmission.

35. The method of claim 34 wherein said step of making a portion of said first chamber wall resistant to heat transmission comprises the step of applying a heat-insulating material to said first chamber wall to make said first chamber wall resistant to heat transmission.

36. The method of claim 34 wherein said step of making a portion of said first chamber wall resistant to heat transmission comprises the step of applying a heat-reflective surface to said first chamber wall to make said first chamber wall resistant to heat transmission.

37. A method of heating tissue from within a duct in a patient's body, comprising the steps of inserting into the duct a plurality of fluid-expandable chambers, each of said chambers being defined at least in part by a flexible wall that engages body tissue, said plurality of chambers being fillable with fluid through a plurality of lumens extending through a catheter shaft on which said chambers are mounted, at least a first of said chambers being fillable with fluid separately with respect to at least a second of said chambers, so that said plurality of chambers can occupy any of a plurality of possible total volumes, selecting one of said possible total volumes, filling at least one of said chambers with fluid, while leaving at least one other of said chambers unfilled, so that said plurality of chambers occupies said selected total volume, and heating said fluid within at least one of said chambers, so that heat of a controlled temperature is transmitted from said fluid to surrounding tissue by thermal conduction through a wall of said at least one of said chambers, whereby compression of said tissue is controlled, and hence effectiveness of transfer of heat to said tissue is controlled.

* * * * *